United States Patent
Sweeney

(10) Patent No.: US 11,896,501 B2
(45) Date of Patent: Feb. 13, 2024

(54) EXPANDABLE IMPLANT EXPANSION DRIVER

(71) Applicant: NuVasive, Inc., San Diego, CA (US)

(72) Inventor: Thomas Sweeney, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 18/146,179

(22) Filed: Dec. 23, 2022

(65) Prior Publication Data

US 2023/0139238 A1    May 4, 2023

Related U.S. Application Data

(63) Continuation of application No. 16/997,870, filed on Aug. 19, 2020, now Pat. No. 11,554,025.

(60) Provisional application No. 62/888,976, filed on Aug. 19, 2019.

(51) Int. Cl.
| | |
|---|---|
| *A61F 2/46* | (2006.01) |
| *A61F 2/44* | (2006.01) |
| *F16H 1/22* | (2006.01) |
| *A61F 2/30* | (2006.01) |

(52) U.S. Cl.
CPC ............ *A61F 2/4611* (2013.01); *A61F 2/442* (2013.01); *F16H 1/222* (2013.01); *A61F 2/4455* (2013.01); *A61F 2002/30523* (2013.01); *A61F 2002/30579* (2013.01); *A61F 2002/4627* (2013.01)

(58) Field of Classification Search
CPC ...... A61F 2/4611; A61F 2/442; A61F 2/4455; A61F 2002/30523; A61F 2002/30579; A61F 2002/4627; F16H 1/222

USPC ............................................. 623/17.11–17.16
See application file for complete search history.

(56) References Cited

U.S. PATENT DOCUMENTS

| | | | | |
|---|---|---|---|---|
| 5,647,254 | A | * | 7/1997 | Cook, Jr. .............. B25B 23/145 81/475 |
| 6,126,665 | A | * | 10/2000 | Yoon .................... A61B 17/062 606/144 |
| 8,636,746 | B2 | | 1/2014 | Jimenez et al. |
| 10,702,396 | B2 | | 7/2020 | Burrows-Ownbey et al. |
| 11,298,243 | B2 | | 4/2022 | Himmelberger et al. |
| 2006/0155297 | A1 | * | 7/2006 | Ainsworth ........... A61B 17/025 606/99 |
| 2007/0123905 | A1 | | 5/2007 | Schneid |
| 2009/0292361 | A1 | | 11/2009 | Lopez |
| 2010/0016971 | A1 | * | 1/2010 | Berry .................... A61F 2/4611 623/17.15 |
| 2010/0160984 | A1 | | 6/2010 | Berry et al. |
| 2015/0066145 | A1 | * | 3/2015 | Rogers .................. A61F 2/4611 623/17.15 |
| 2015/0101432 | A1 | * | 4/2015 | Gao ........................ B25B 17/02 74/405 |
| 2016/0167205 | A1 | * | 6/2016 | Wang ..................... B25B 15/04 81/58.3 |

(Continued)

*Primary Examiner* — Jessica Weiss

(57) ABSTRACT

This disclosure includes an expansion driver for adjusting expandable implants, the expansion driver including: a first driver having a first gear disposed at a first end thereof; and a second driver having a second gear disposed at a first end of the second driver; and a handle operably connected to the first driver and the second driver, the handle having at least one bevel gear rotatably attached thereto, the at least one bevel gear engaging each of the first gear and the second gear; wherein upon a rotation of the handle a torque is applied to at least one of the first driver or the second driver.

18 Claims, 7 Drawing Sheets

(56) References Cited

U.S. PATENT DOCUMENTS

| | | | |
|---|---|---|---|
| 2017/0071753 A1* | 3/2017 | Josse | A61F 2/4637 |
| 2018/0125677 A1 | 5/2018 | Burrows-Ownbey et al. | |
| 2019/0038283 A1* | 2/2019 | Shelton, IV | A61B 34/30 |
| 2021/0045891 A1* | 2/2021 | Rogers | A61F 2/4455 |
| 2021/0346174 A1* | 11/2021 | Flint | A61F 2/4611 |
| 2022/0015922 A1 | 1/2022 | Rogers et al. | |

* cited by examiner

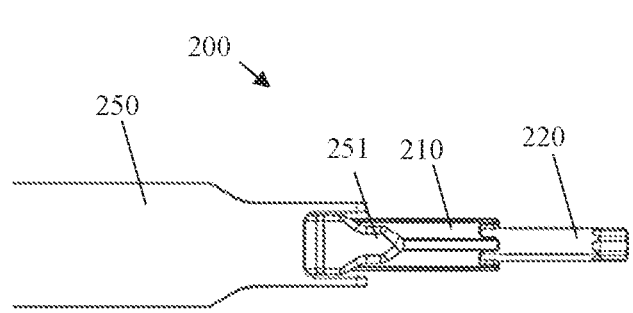
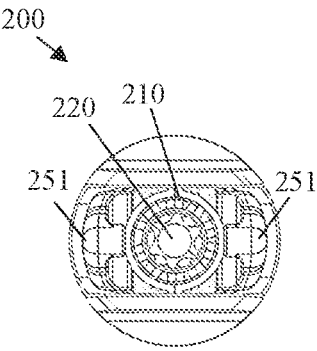
FIG.6                FIG.7
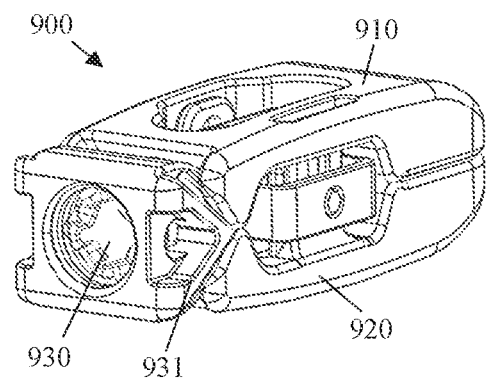
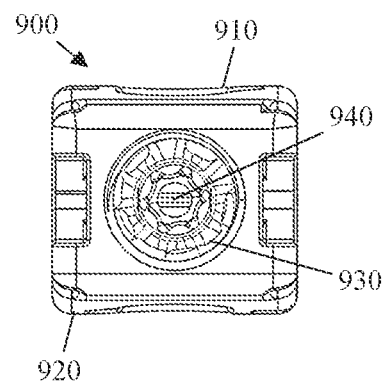
FIG.8                FIG.9
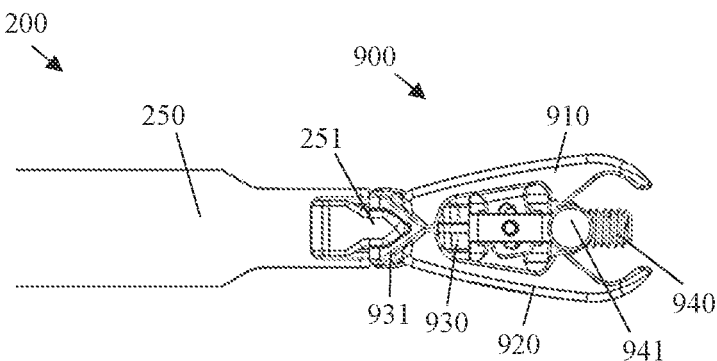
FIG.10

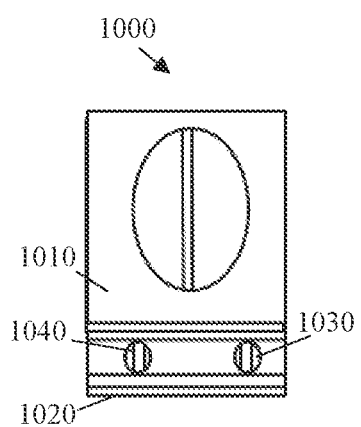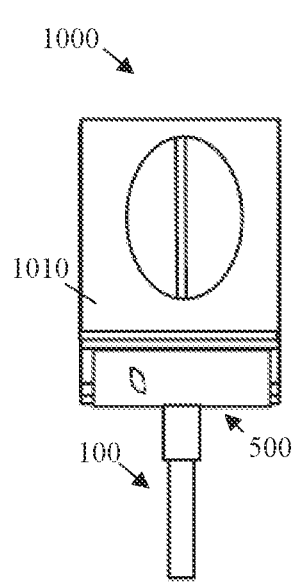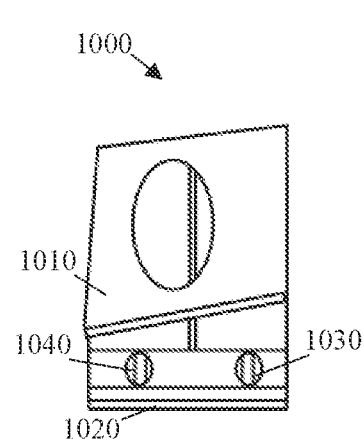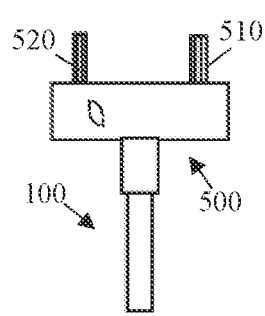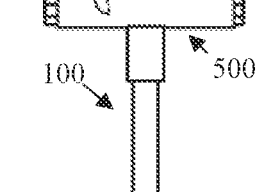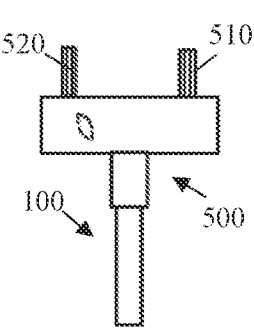
FIG.16   FIG.17   FIG.18

** # EXPANDABLE IMPLANT EXPANSION DRIVER

CROSS-REFERENCE TO RELATED APPLICATIONS

This application is a continuation of U.S. application Ser. No. 16/997,870, filed Aug. 19, 2020, which claims the benefit of the filing date of U.S. Provisional Application No. 62/888,976 which was filed on Aug. 19, 2019. The contents of each of the foregoing applications are incorporated by reference in their entirety as part of this application.

BACKGROUND OF THE INVENTION

Field of the Invention

The present disclosure relates generally to medical devices, and more particularly to an instrument for use with expandable implants.

Description of the Related Art

Back problems are one of the most common and debilitating occurrences. In the United States alone, over 500,000 spine lumbar and cervical fusion procedures are performed each year. One of the causes of back pain and disability results from the rupture or degeneration of one or more intervertebral discs in the spine.

Surgical procedures are commonly performed to correct problems with displaced, damaged, or degenerated intervertebral discs due to trauma, disease or aging. Generally, spinal fusion procedures involve removing some or all of the diseased or damaged disc, and inserting one or more intervertebral implants into the resulting disc space. Anterior lumbar interbody fusion (ALIF), lateral lumbar interbody fusion, e.g. XLIF® (NuVasive, Inc., San Diego, CA), and transforaminal lumbar interbody fusion (TLIF) are techniques that spine surgeons use to access the portions of the spine to be repaired or replaced.

Replacement of injured or deteriorated spinal bone with artificial implants requires a balance of knowledge of the mechanisms of the stresses inherent in the spine, as well as the biological properties of the body in response to the devices. Further, the size, configuration, and placement of an artificial implant requires precision positioning and handling by a skilled surgeon.

SUMMARY OF THE INVENTION

This disclosure includes instruments for expandable implants and methods of using the same.

In some embodiments, the instrument includes: a first driver having a first gear disposed at a first end thereof; and a second driver having a second gear disposed at a first end of the second driver; and a differential operably connected to the first driver and the second driver, the differential engaging each of the first gear and the second gear and configured to transfer a torque to at least one of the first driver and the second driver.

In some embodiments, a differential for expansion drivers may include: at least one bevel gear, a first drive gear connected to a first output shaft, and a second drive gear connected to a second output shaft, the at least one bevel gear rotatably connected to a first drive source and configured to rotate around a first axis, wherein upon a rotation of the at least one bevel gear about the axis by the drive source, a torque will be transferred from the at least one bevel gear to one or more of the first drive gear and the second drive gear.

In some embodiments, a differential for expansion drivers may include: a first drive gear connected to a first output shaft configured to rotate around a first axis, a second drive gear connected to a second output shaft configured to rotate around the first axis, and a rotating carrier rotatably connected to a first drive source and configured to rotate around the first axis, wherein upon a rotation of rotating carrier about the axis, a torque will be transferred from the rotating carrier to one or more of the first drive gear and the second drive gear.

In some embodiments, the instrument includes: a first driver having a first gear disposed at a first end thereof; and a second driver having a second gear disposed at a first end of the second driver; and a handle operably connected to the first driver and the second driver, the handle having at least one bevel gear rotatably attached thereto, the at least one bevel gear engaging each of the first gear and the second gear; wherein upon a rotation of the handle a torque is applied to at least one of the first driver or the second driver.

In some embodiments, the instrument includes: a first driver having a first gear disposed at a first end thereof; a second driver, at least a portion of the second driver extending axially through the first driver, and a second gear disposed at a first end of the first driver, the second gear opposing the first gear; and a handle operably connected to the first driver and the second driver, the handle having a first bevel gear and a second bevel gear rotatably attached thereto, the first bevel gear and the second bevel gear each configured to communicate with the first gear and the second gear; wherein upon a rotation of the handle a torque is configured to be transferred to at least one of the first driver and the second driver.

In some embodiments, the expansion driver includes: a first driver having a first end and a second end, with a first gear disposed at the first end and the second end configured to mate with a first lead screw of an expandable implant; a second driver having a first end and a second end, a second gear disposed at the first end and configured to oppose the first gear of the first driver, at least a portion of the second end of the second driver extending axially through at least a portion of the first driver and configured to mate with a second lead screw of the expandable implant; and a handle operably connected to the first driver and the second driver, the handle having a first bevel gear and a second bevel gear rotatably attached thereto, the first bevel gear and the second bevel gear each configured to communicate with the first gear and the second gear; wherein upon a rotation of the handle the torque is configured to be transferred from the handle to the first bevel gear and the second bevel gear, with the first bevel gear and the second bevel gear configured to rotate at least one of the first driver and the second driver.

In some embodiments, the expansion driver includes: a first driver having a first end and a second end, with a first gear disposed at the first end and the second end configured to mate with a first lead screw of an expandable implant; a second driver having a first end and a second end, a second gear disposed at the first end and configured to oppose the first gear of the first driver, at least a portion of the second end of the second driver extending axially through at least a portion of the first driver and configured to mate with a second lead screw of the expandable implant; and a handle operably connected to the first driver and the second driver, the handle having a rotating carrier attached thereto, the rotating carrier configured to communicate with the first gear and the second gear; wherein upon a rotation of the handle the torque is configured to be transferred from the handle to the rotating carrier, with the rotating carrier configured to rotate at least one of the first driver and the second driver.

In some embodiments, a splitter attachment for an expansion driver includes an input configured to interface with an expansion driver, a first splitter output shaft configured to rotate a first actuator of an expandable implant, and a second splitter output shaft configured to rotate a second actuator of the expandable implant, wherein the splitter attachment is configured to transfer torque from the expansion driver to at least one of the first splitter output shaft and the second splitter output shaft.

An exemplary method of treating a spinal deformity is provided, the method including: preparing an intervertebral disc space of a patient; placing an expandable implant within the prepared intervertebral disk space of the patient; adjusting the expandable implant using an expansion driver having: a first driver, a second driver, and at least one bevel gear, wherein the at least one bevel gear is configured to rotate at least one of the first driver or the second driver to adjust the expandable implant.

BRIEF DESCRIPTION OF THE DRAWINGS

These and other features may be further understood by those with skill in the art upon a review of the appended drawings, wherein:

FIG. 6 shows a tip of an expansion driver in accordance with a second embodiment, the tip configured to interface with an expandable implant;

FIG. 7 shows a front view of the expansion driver configured to interface with the expandable implant;

FIG. 8 shows a rear perspective view an expandable implant in accordance with a first embodiment;

FIG. 9 shows a rear view of the expandable implant;

FIG. 10 shows the tip of the expansion driver in accordance with the second embodiment, the tip removably secured to and adjusting the expandable implant;

FIG. 16 shows an expandable implant and an expansion driver integrated with the splitter attachment and configured to adjust the expandable implant;

FIG. 17 shows the expandable implant being adjusted by the expansion driver integrated with the splitter attachment; and FIG. 18 shows the expandable implant adjusted to an exemplary angle of lordosis, with the expansion driver having the splitter attachment removed from the expandable implant.

DETAILED DESCRIPTION

Figure 1:
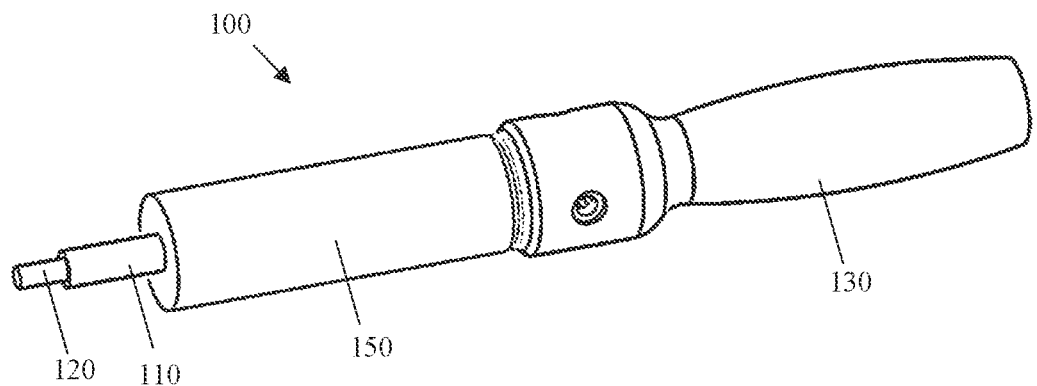
FIG. 1 shows a perspective view of an expansion driver in accordance with a first embodiment.

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure.

Expandable implants may include: intervertebral cages, plates, distraction rods, and other adjustable medical device. Some expandable implants may include for example: an upper endplate, a lower endplate, and an actuator configured to change a dimension of the expandable implant. The change of dimension of the expandable implant may include, a change in height, a change in width, a change in length, and a change in an angle of lordosis.

In some embodiments, an expandable implant may be designed to be inserted into the intervertebral disc space between a patient's adjacent vertebral bodies using e.g. a lateral or posterior approach among others. Expandable implants are generally made of any suitable biocompatible material or combination of materials. For example, the implant components may include one or more of: metal, thermoplastics such as poly ether ether ketone (PEEK), and a combination of the metal and PEEK. The expandable implant may be configured to be inserted into the disc space in a first collapsed configuration, and upon being placed in a desired location within the disc space, the expandable implant may be adjusted in one or more of a height, width, length, and an angle of lordosis. For example: the anterior height of the implant may be greater than the posterior height of the implant, thereby restoring a more natural lordotic curvature of a particular segment of the lumbar spine.

Adjustment of expandable implants may be accomplished for example by engaging an actuator with an expansion driver to activate the actuator and cause a movement of the first endplate relative to the second endplate to change one or more of a height, a width, a length, and an angle of lordosis of the expandable implant. The actuator may include, for example, at least one actuator and at least one translating wedge configured to move along the length of the at least one actuator upon a rotation of the actuator, with the wedge configured to move one or more of the first endplate and the second endplate relative to each other, to thereby change one or more of a height and an angle of lordosis of the expandable implant.

In some embodiments, the actuator of the expandable implant may include two or more actuators. In some embodiments, a first actuator is axially accessible to an expansion driver through a hollow opening in a second actuator. In other embodiments, the first actuator is disposed in an anterior portion of the implant and the hollow second actuator is disposed in an anterior portion of the implant. In some embodiments the second actuator is annularly and rotatably disposed around the first actuator. And in some embodiments, as disclosed below, the first actuator and the second actuator may not be coaxial, rather for example parallel, and may be separated by a distance. All various placements known and used in the art are hereby contemplated and incorporated.

Adjustment of expandable spinal implants may require an expansion driver. The expansion driver described herein is capable of delivering one or more of simultaneous and equal amounts of torque to both a first actuator and a second actuator of an expandable implant that has two independent expansion mechanisms to allow for independent expansion of a first portion and a second portion of the implant.

According to an exemplary embodiment, the expansion driver has two or more coaxial driver shafts and a handle. The handle and the two or more coaxial driver shafts are operably coupled by a differential for an expansion driver. A differential for an expansion driver may include: at least one bevel gear, a first drive gear connected to a first output shaft, and a second drive gear connected to a second output shaft. The at least one bevel gear may be rotatably connected to a first drive source and configured to rotate around a first axis. The teeth of the at least one bevel gear may be simultaneously in communication with the teeth of the first drive gear and the second drive gear. Upon a rotation by the drive source of the at least one bevel gear, a torque may be transferred from the first drive source to the at least one bevel gear, and to one or more of the first drive gear and the second drive gear. If the first output shaft is experiencing a greater input resistance than the second output shaft, the torque of the at least one bevel gear will be transferred to the second drive gear of the second output shaft. If the second output shaft is experiencing a greater input resistance than the first output shaft, the torque of the at least one bevel gear will be transferred to the first drive gear of the first output shaft. If the input resistance is substantially equal on the first output shaft and the second output shaft, the torque of the at least one bevel gear will be transferred to both the first drive gear of the first output shaft and the second drive gear of the second output shaft. This can be explained in that the torque effectively chooses the gear of least resistance, and where all else is the same, drives both the first gear and the second gear.

As one with skill in the art may appreciate, a bevel gear may include a pinion and any type of known gear, and more gearing may be added to step up or step down the output torque of one or more of the first drive shaft and the second drive shaft. For example, one or more additional gears may be added between the first drive gear and the first output shaft to increase an amount of torque outputted at the first output shaft. Similarly, one or more additional gears may be added between the second drive gear and the second output shaft to increase an amount of torque outputted at the second output shaft.

Additionally, in some embodiments, the differential may include an epicyclic differential, a spur-gear differential, an active differential, a passive differential, and any differential known and used in the art.

FIGS. 1-5 show an expansion driver 100 including: a first driver 110 having a first gear 111 disposed at a first end thereof; a second driver 120, at least a portion of the second driver 120 extending axially through the first driver 110, and a second gear 121 disposed at a first end of the second driver 120, the teeth of the second gear 121 facing in a direction opposing the teeth of the first gear 111; and a handle 130 operably connected to the first driver 110 and the second driver 120, the handle 130 having a first bevel gear 132 and a second bevel gear 133 rotatably attached thereto, the first bevel gear 132 and the second bevel gear 133 each configured to communicate with the first gear 111 and the second gear 121; wherein upon a rotation of the handle 130 a torque is configured to be transferred to at least one of the first driver 110 and the second driver 120.

In FIG. 1 the expansion driver 100 is shown including a housing 150 configured to enclose at least a portion of the first driver 110 and at least a portion of the second driver 120. In some embodiments, the housing 150 of the expansion driver 100 may be configured to removably secure an expandable implant to the distal end of the expansion driver 100 via, for example, tabs or other projections extending from the distal end of the housing and configured to engage an expandable implant 900 (see, FIGS. 8-10).

The expansion driver 100 is configured to adjust an expandable implant 900 having a first actuator 930 disposed at a first end of the expandable implant 900 and a second actuator 940 disposed at a second end of the expandable implant 900, with the first actuator 930 hollow and configured to receive at least a portion of the second driver 120 therethrough allowing the second driver 120 access to adjust the second actuator 940. The first driver 110 is configured to communicate with the first actuator 930 and rotate the first actuator 930 upon a rotation of the first driver 110. The second driver 120 is configured to communicate with the second actuator 940 and rotate the second actuator 940 upon a rotation of the second driver 120. In both cases, rotation of either actuator is configured to cause movement of the first endplate 910 of the expandable implant 900 relative to second endplate 920 to change one or more of a height, a width, a length, and an angle of lordosis of the expandable implant 900.

The expansion driver 100 is configured such that, upon activation of the drive source which includes the rotation of the handle 130, a torque is transferred from the handle 130 to at least one of a first bevel gear 132 and a second bevel gear 133, with the first bevel gear 132 and the second bevel gear 133 configured to rotate one or more of the first driver 110 and the second driver 120, depending on an amount of resistance on the first actuator and the second actuator of the expandable implant 900.

Expandable implants 900 placed between vertebral bodies of a patient experience numerous forces, particularly during adjustment. As one with skill in the art may appreciate, in an expandable implant 900 having an actuator including a first actuator 930 and a second actuator 940, each actuator is going to experience a different amount of resistance upon adjustment which depends on the instantaneous load and state of the vertebral bodies relative to the expandable implant 900. When driving the first actuator 930 and the second actuator 940 using a fixed expansion driver, for example, unequal resistance can result in uneven adjustment of the expandable implant 900. In the instant embodiment however, the first bevel gear 132 and the second bevel gear 133 allow for selective driving by the expansion driver to ensure an equal amount of torque is delivered.

For example, when a first amount of resistance from the first actuator 930 on the first driver 110 is less than a second amount of resistance from the second actuator 940 on the second driver 120, the first bevel gear 132 and the second bevel gear 133 are configured to rotate the first driver 110. The first driver 110 will in turn rotate the first actuator 930 to thereby adjust the expandable implant 900. The second driver 120 will not adjust the second actuator 940, and thus the first actuator 930 will continue to be rotated adjusting the angle of lordosis of the expandable implant 900 until a substantially equal amount of resistance is observed by the first actuator 930 and the second actuator 940.

When a first amount of resistance from the first actuator 930 on the first driver 110 is more than a second amount of resistance of the second actuator 940 on the second driver 120, the first bevel gear 132 and the second bevel gear 133 are configured to rotate the second driver 120. The second driver 120 will in turn rotate the second actuator 940 to thereby adjust the expandable implant 900. The first driver 110 will not adjust the first actuator 930, and thus the second actuator 940 will continue to be rotated, adjusting the angle of lordosis of the expandable implant 900 until a substantially equal amount of resistance is observed by the first actuator 930 and the second actuator 940.

When a first amount of resistance from the first actuator 930 on the first driver 110 is substantially equal to a second amount of resistance of the second actuator 940 on the second driver 120, the first bevel gear 132 and the second bevel gear 133 are configured to rotate both the first driver 110 and the second driver 120. The first driver 110 will in turn rotate the first actuator 930, the second driver 120 will in turn rotate the second actuator 940, and both actuators will simultaneously adjust the expandable implant 900. As one with skill in the art may appreciate, in the instant embodiment of an expandable implant 900 simultaneous adjustment of the first actuator 930 and the second actuator 940 will result in a change in height of the expandable implant 900.

Figure 2:
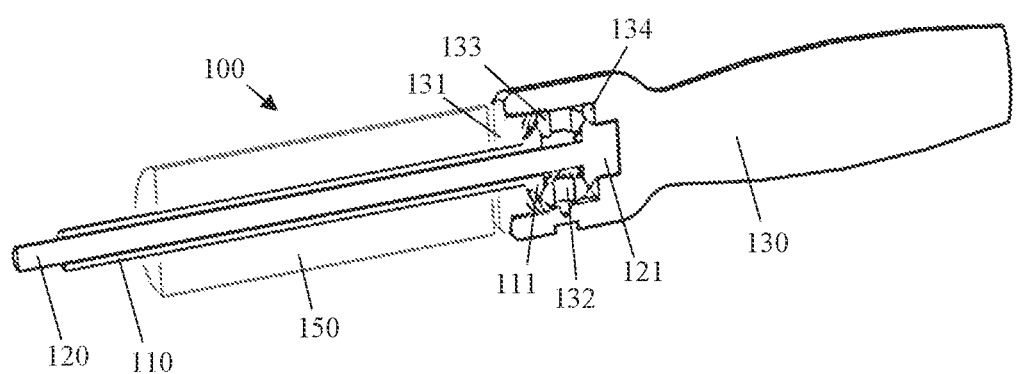
FIG. 2 shows a cross-sectional view of the expansion driver in accordance with the first embodiment.

As shown in FIG. 2, the expansion driver 100 includes: the first driver 110 having a first gear 111 disposed at a first end thereof; a second driver 120, at least a portion of the second driver 120 extending axially through a hollow cavity of the first driver 110, and a second gear 121 disposed at a first end of the second driver 120, the teeth of the second gear 121 opposing the teeth of the first gear 111; and a handle 130 operably connected to the first driver 110 and the second driver 120, the handle 130 having a first bevel gear 132 and a second bevel gear 133 rotatably attached thereto, the teeth of the first bevel gear 132 and the teeth of the second bevel gear 133 configured to communicate with the first gear 132 of the first driver 110 and the second gear 133 of the second driver 120; wherein upon a rotation of the handle 130 a rotational torque is configured to be transferred to at least one of the first driver 110 and the second driver 120.

The housing 150 of the expansion driver 100 is configured to enclose at least a portion of the first driver 110 and the second driver 120 within a cavity of the handle 130. The expansion driver 100 also includes a threaded cap 131 configured to communicate with a threaded surface of the cavity of the handle 130 to secure the first end of the first driver 110, the first end of the second driver 120, the first gear 111, the second gear 121, the first bevel gear 132 and the second bevel gear 133 within an interior cavity 134 of the handle 130.

The first bevel gear 132 and the second bevel gear 133 may be rotatably disposed within the interior cavity 134 of the handle 130, and rotatably secured to a sidewall of the cavity 134 by for example a pin. At least a portion of the surface of the interior cavity 134 may be threaded.

Figure 3:
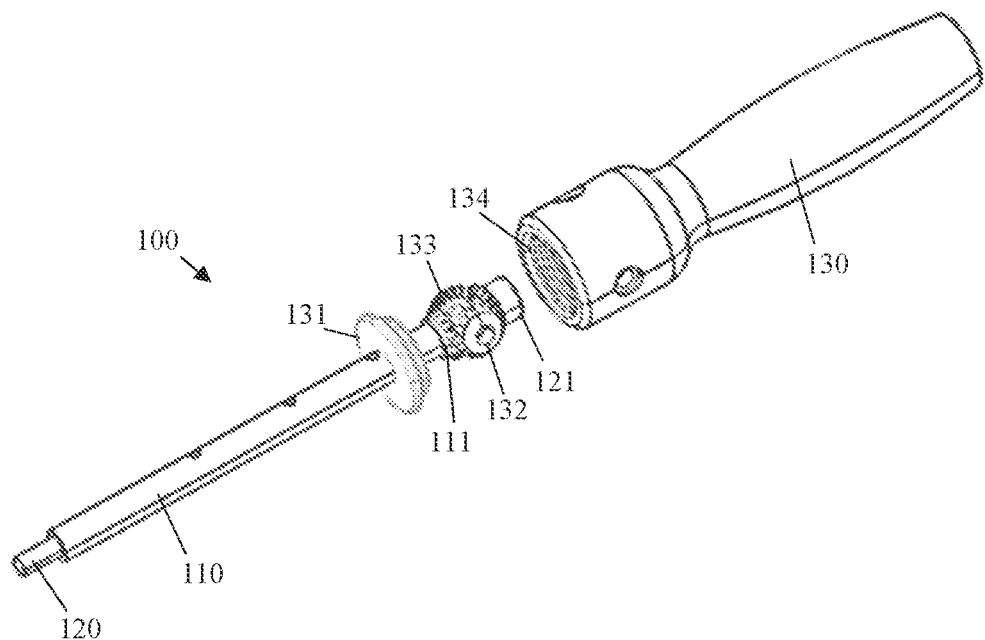
FIG. 3 shows perspective view of the expansion driver in accordance with the first embodiment, the housing removed revealing some of the internal components of the expansion driver.

In FIG. 3, the expansion driver 100 is shown in a partially exploded view with the housing 150 revealing an interface of the first driver 110 and the second driver 120 including the first bevel gear 132 and the second bevel gear 133 of the handle 130 which forms a differential for the expansion driver. The first driver 110 has a first end and a second end, with a first gear 111 disposed at the first end of the first driver 110 a second end opposite the first end that is configured to mate with a head of a first actuator 930 of an expandable implant 900. The second driver 120 includes a first end and a second end, a second gear 121 disposed at the first end, the teeth of which are facing in the opposite direction of the teeth of the first gear 111 of the first driver 110, with at least a portion of the second end of the second driver 120 extending axially through at least a portion of the first driver 110 and the second end of the second driver 120 configured to mate with a second actuator 940 of the expandable implant 900. The handle 130 includes a threaded cavity 134 configured to receive at least a portion of the first driver 110 and the second driver 120, the handle 130 having the first bevel gear 132 and the second bevel gear 133 rotatably attached thereto, the first bevel gear 132 and the second bevel gear 133 each configured to communicate with the first gear 111 and the second gear 121; wherein upon a rotation of the handle 130 a rotational torque is configured to be transferred from the handle 130 to the first bevel gear 132 and the second bevel gear 133, with the first bevel gear 132 and the second bevel gear 133 rotatably secured to the handle 130 and configured to communicate with the first gear 111 and the second gear 121 to rotate at least one of the first driver 110 and the second driver 120, and thereby configured to adjust an expandable implant 900.

Figure 4:
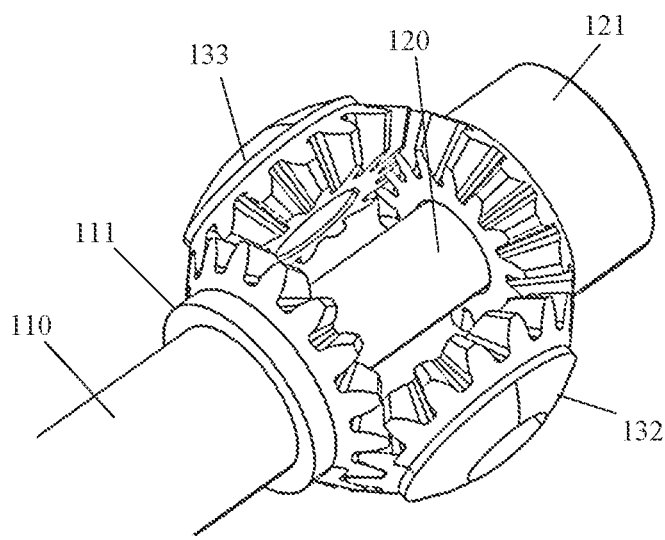
FIG. 4 shows the differential including a first gear of the first driver, a second gear of the second driver, and at least one bevel gear of the handle.

FIG. 4 shows an enhanced view of the differential of the expansion driver formed between the first gear 111 of the first driver 110, the second gear 121 of the second driver 120, the first bevel gear 132, and the second bevel gear 133 which form a differential gear set for the expansion driver 100. The teeth of the first gear 111 mirror the teeth of the second gear 121, whereby both the first gear 111 and the second gear 121 can simultaneously communicate with each of the at least one bevel gears 132, 133.

As one with skill in the art may appreciate, a rotation of the handle 130 drives the first bevel gear 132 and the second bevel gear 133 to rotate around the axis of the first driver 110 and the second driver 120. The teeth of the first bevel gear 132 and the second bevel gear 133 communicate with the teeth of the first gear 111 and the teeth of the second gear 121. Depending on a comparison of an amount of resistance experienced by each of the first driver 110 and the second driver 120 at the first and second actuators 930,940, respectively, of the expandable implant 900, the first bevel gear 132 and the second bevel gear 133 will rotate whichever of the first driver 110 and the second driver 120 is experiencing the least amount of resistance. In the condition in which the amount of resistance is substantially equal, the first bevel gear 132 and the second bevel gear 133 will drive both the first driver and the second driver equally.

In the illustrated embodiment exemplary embodiment, two bevel gears are shown. However as one with skill in the art may appreciate, depending on the needs of a designer, a differential for expansion drivers may be formed by one, two, three, or any number of bevel gear gears. The bevel gear gears may be directly in contact with one or more of the first gear and second gear associated with the output drivers. Other known gearing configurations of known differentials are contemplated herein for use with expansion drivers and the use of which is intended to be incorporated within this disclosure.

Figure 5:
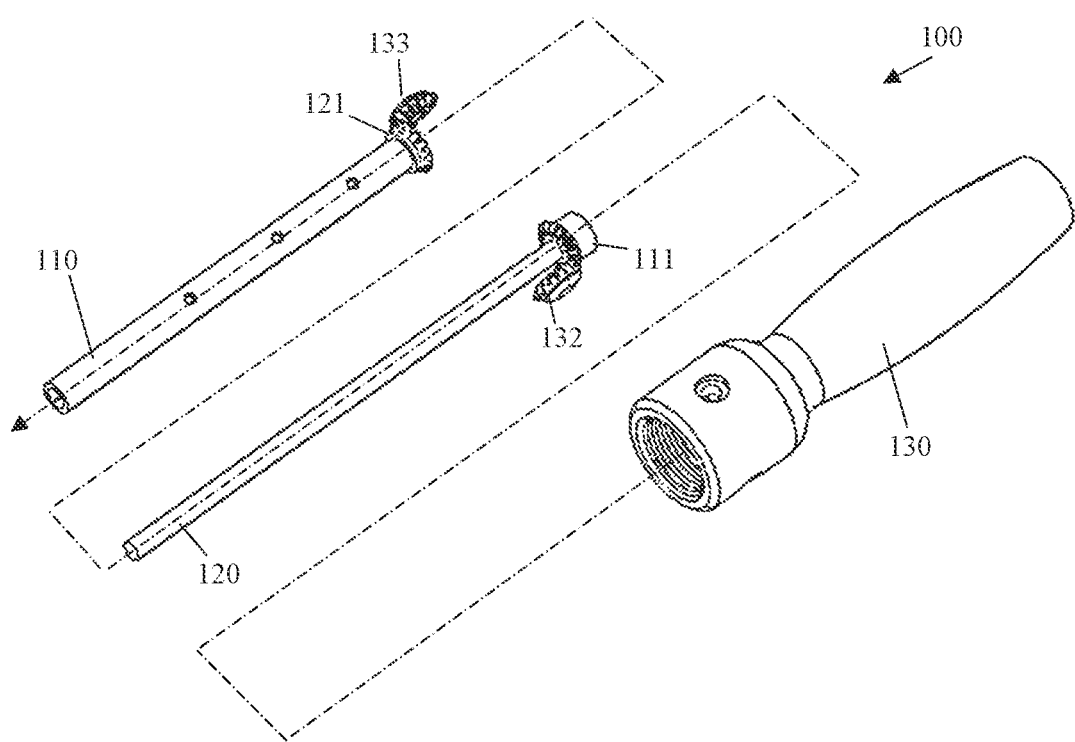
FIG. 5 shows an exploded view of the expansion driver in accordance with the first embodiment.

FIG. 5 shows an exploded view of the expansion driver 100 in accordance with the first embodiment, and illustrates an exemplary method of assembly thereof. The first driver 120 is hollow and has a cannula configured to receive at least a portion of the second driver 110, therethrough. The first bevel gear 132 and the second bevel gear 133 are configured to communicate with the first gear 111 of the first driver 110 and the second gear 121 of the second driver 120, while being rotatable disposed within the cavity of the handle 130.

Some or all of the components may be fabricated using known machining and additive manufacturing techniques. The drivers may be fabricated from known biocompatible materials including: aluminum, steel, and titanium. Additionally, the handle may be fabricated from materials including: a polymeric material, carbon fiber, and metals.

FIG. 6 shows a side view of a tip of an expansion driver 200 in accordance with an exemplary embodiment. The expansion driver 200 may include some or all of the features from the first embodiment, and is also shown including a first driver 210 and a second driver 220. The first driver 210 is configured to interface with a first actuator 930 of an expandable implant 900, and is configured to rotate independently around the second driver 220. The second driver 220 is configured to interface with a second actuator 940 of the expandable implant 900, and is configured to rotate independently within the first driver 210. The second ends of the first driver 210 and the second driver 220 may be profiled or keyed to communicate with a complementary contact surface of one or more of: the first actuator 930 and the second actuator 940 of the expandable implant 900.

The housing 250 of the expansion driver 200 is shown including locking tabs 251 configured to removably secure an expandable implant 900 to the expansion driver 200. In some embodiments, the expandable implant 900 is removably secured to the expansion driver 200 prior to placement in the intervertebral space of the patient, with the expansion driver 200 configured to insert, place, and adjust a dimension of the expandable implant 900 within the intervertebral space of the patient.

FIG. 7 shows a front view of the expansion driver 200, looking down the axis of the first driver 210 and the second driver 120. With the first driver 210 annularly disposed around the second driver 220. The first driver 210 is configured to rotate independently of the second driver 220 to drive the first actuator 930 of the expandable implant 900. The second driver 220 is configured to rotate independently of the first driver 210, and configured to adjust the second actuator 940 of the expandable implant 900. The housing 250 is shown including the two locking tabs 251 configured to removably secure the expandable implant 900 to the expansion driver 200.

FIG. 8 shows a rear perspective view of an embodiment of an expandable implant 900. The expandable implant 900 includes a first endplate 910, a second endplate 920, a first translating member 931 configured to translate along the length of a first actuator 930, and a second translating 941 member configured to translate along the length of a second actuator 940, wherein translation of one or more of the first translating member 931 and the second translating member 941 is configured to change at least one of a height and an angle of lordosis of the expandable implant 900.

FIG. 9 shows a rear view of the expandable implant 900. The first actuator 930 and second actuator 940 are each configured to interface with each of the first driver 220 and second driver 210 of the expansion driver 200 respectively. The first actuator 930 is hollow and configured to receive at least a portion of the second driver 220 there through. The first actuator 930 is configured to communicate with the first driver 210, and the second actuator 940 is configured to receive and communicate with the second driver 220 to adjust the expandable implant 900.

FIG. 10 shows the expandable implant 900 secured to the expansion driver 200, with the expandable implant 900 shown being adjusted to an exemplary angle of lordosis. The expandable implant 900 is removably secured to the expansion driver 200 by locking tabs 251. The expandable implant 900 is shown in FIG. 10 in a second adjusted configuration being adjusted to some exemplary angle of lordosis.

According to one exemplary method of adjusting an expandable implant 900, the steps may include: preparing an intervertebral disc space of a patient; placing an expandable implant 900 within the prepared intervertebral disk space of the patient; adjusting the expandable implant 900 using an expansion driver 100 having: a first driver 110, a second driver 120, and at least one bevel gear 132, 133, wherein the at least one bevel gear 132, 133 is configured to rotate at least one of the first driver or the second driver to adjust the expandable implant 900.

To prepare the intervertebral disc space of the patient, the surgeon may first gain access to the intervertebral disc space via one or more of for example: an anterior, a lateral, and a posterior approach. The intervertebral disc may be partially or totally removed from the disc space. The contact surfaces of the adjacent vertebral bodies may be prepared to help promote fusion.

The expandable implant 900 may be provided to the disc space by an insertion device, for example: an inserter or the expansion driver 100. First the expandable implant 900 would be removably secured to the expansion device 100. Next the expandable implant 900 would be placed within the prepared intervertebral disc space using, for example, an anterior, posterior, transforaminal or lateral approach. If an inserter was used, the inserter would be removed and an expansion driver 100 would then be secured to the implant and used to adjust the expandable implant 900. Finally, the expandable implant 900 is adjusted to achieve the desired size to restore the intervertebral disc space.

As described above, the expandable implant 900 may be designed to be adjusted in one or more of a height, a length, a width and an angle of lordosis of the expandable implant. The expandable implant 900 may be dimensioned according to the size of the patient. The handle 130 of the expansion driver 100 would be rotated, to adjust the expandable implant 900 to the desired height, length, width, and angle of lordosis. Once the surgeon was satisfied with the amount of adjustment the expansion driver 100 can be removed from the expandable implant 900, and subsequently the patient, whilst leaving the expandable implant 900 adjusted within the intervertebral space of the patient.

It may be desirable for the surgeon to pack one or more of the expandable implant and the intervertebral disc space using a bone graft or bone graft substitute material to promote fusion. Fixation plates may be applied to one or more of the vertebral bodies and the expandable implant to secure the expandable implant within the intervertebral disc space. And finally, all placement and expansion instrumentation may be removed and the access hole closed, to allow for the fusion and healing processes to begin.

It has been shown above that the incorporation of a differential gear set is useful to achieve even adjustment of an expandable implant having coaxial actuators. But if the expandable implant includes two separate actuators spaced apart at some distance, a splitter attachment 500 for the expansion driver 100 may be utilized.

Figure 11:
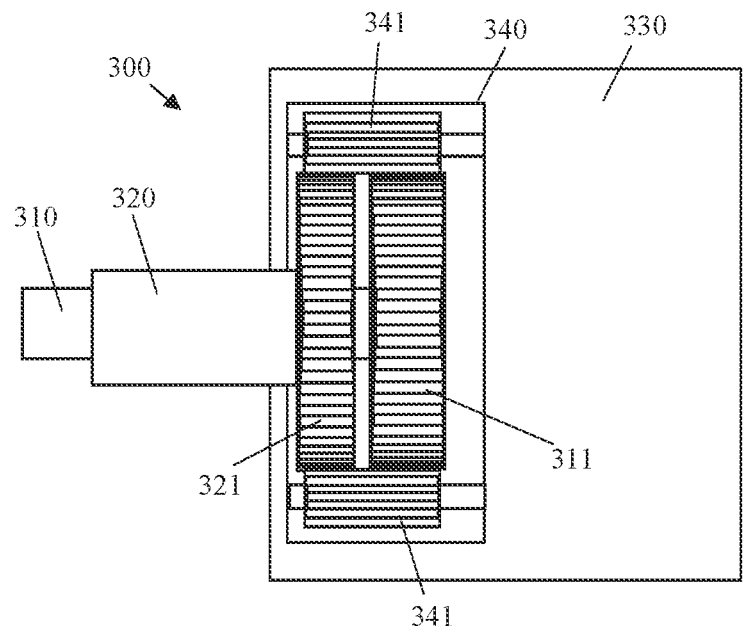
FIG. 11 shows a side view of an expansion driver in accordance with a third embodiment.

FIG. 11 shows a schematic of an expansion driver 300 in accordance with a third embodiment, the expansion driver 300 shown including: a first driver 310 having a first end and a second end, with a first gear 311 disposed at the first end and the second end configured to mate with a first actuator 930 of an expandable implant 900; a second driver 320 having a first end and a second end, a second gear 321 disposed at the first end and configured to oppose the first gear 311 of the first driver 310, at least a portion of the second end of the second driver 320 extending axially through at least a portion of the first driver 310 and configured to mate with a second actuator 940 of the expandable implant 900; and a handle operably 330 connected to the first driver 310 and the second driver 320, the handle having a rotating carrier 340 attached thereto, the rotating carrier 340 which communicates with the first gear 311 and the second gear 321; wherein upon a rotation of the handle 330 a torque is transferred from the handle 330 to the rotating carrier 340, with the rotating carrier 340 having one or more pinion 341 which communicates and rotates at least one of the first driver 310 and the second driver 320.

Figure 12:
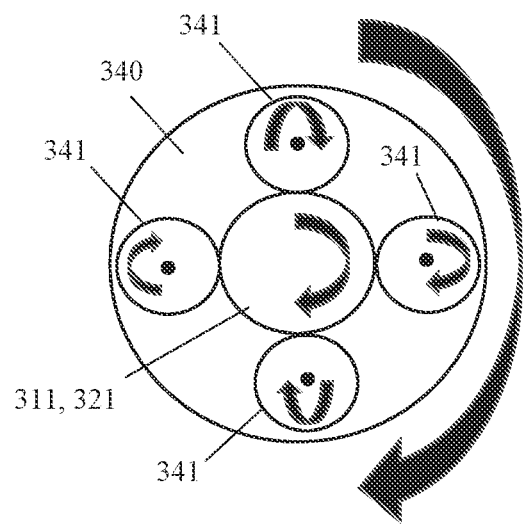
FIG. 12 shows a schematic top view of a rotating carrier of the expansion driver in accordance with the third embodiment of FIG. 11.

The differential gear set of the third embodiment includes a rotating carrier 340. The rotating carrier 340 has at least one pinion 341. In this embodiment there are four individual pinions 341 each configured to communicate with the first gear 311 and the second gear 321. Upon a rotation of the rotating carrier 340 as indicated in FIG. 12, the four pinions 341 will rotate at least one of the first gear 311 and the second gear 321, depending on which is experiencing less input resistance, as discussed above.

Figure 13:
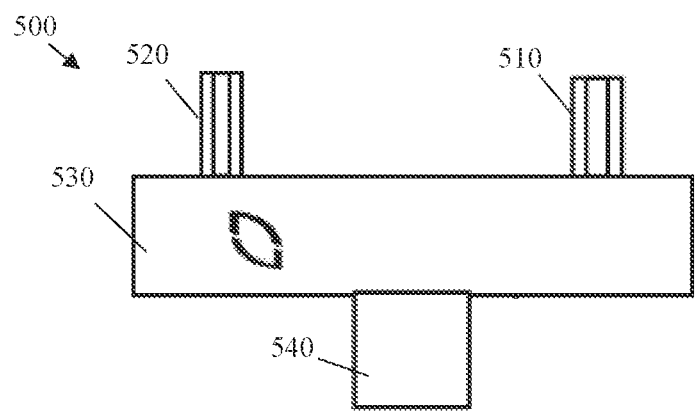
FIG. 13 shows top view of a splitter attachment for an expansion driver in accordance with a first embodiment.

FIG. 13 shows a splitter attachment 500 for the expansion driver 100, the splitter attachment 500 is configured to receive at least a portion of the expansion driver 100 in an input 540 thereof. The splitter attachment 500 includes a first output shaft 510 configured to rotate a first actuator 1030 of an expandable implant 1000 in accordance with a second embodiment, and a second output shaft 520 configured to rotate a second actuator 1040 of the expandable implant 1000.

Figure 14:
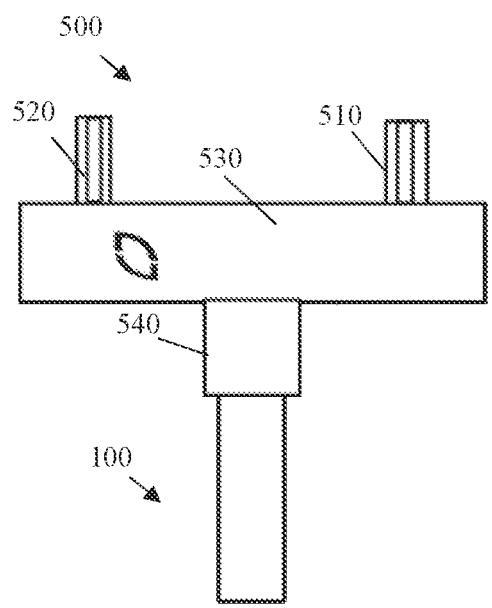
FIG. 14 shows the splitter attachment integrated with an expansion driver.

FIG. 14 shows the expansion driver 100 in communication with the splitter attachment 500. The splitter attachment 500 configured to separate the torque of the first driver 110 and second driver 120 of the expansion driver 100 from a coaxial rotation into two parallel splitter output shafts 510, 520 separated by a distance. The splitter attachment 500 enables the expansion driver 100, to deliver an equal amount of torque and adjustment to an expandable implant 1000 having two non-coaxial actuators separated by a distance.

Figure 15:
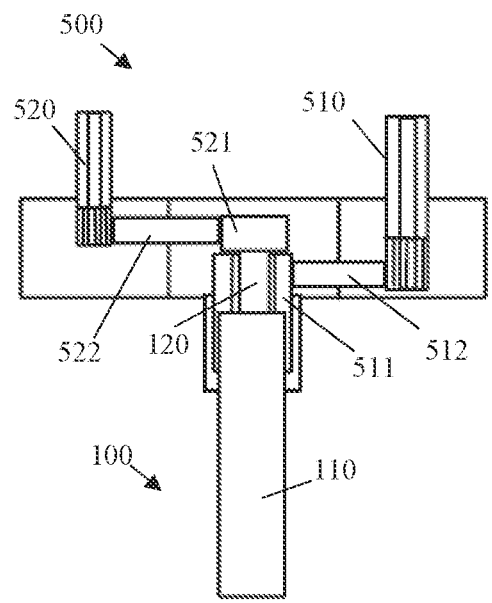
FIG. 15 shows a cross-sectional view of the splitter attachment integrated with an expansion driver.

FIG. 15 shows a cross-sectional view of the expansion driver 100 in communication with the splitter attachment 500. The splitter attachment 500 includes a first coupler gear 511 configured to operably mate with the first driver 110 and rotatably disposed within a housing 530 of the splitter attachment 500. The splitter attachment 500 also includes a first transfer gear 512 configured to rotate and transfer torque from the first coupler gear 511 to a first splitter output shaft 510. As one with skill in the art may appreciate additional gears and shafts may be provided in accordance with known methods of stepping up the output torque, stepping down the output torque, and changing the distance separating the first splitter output shaft 510 and the second splitter output shaft 520.

The splitter attachment 500 includes a second coupler gear 521 configured to operably mate with the second driver 120 and rotatably disposed within the housing 530 of the splitter attachment 500. The splitter attachment 500 also includes a second transfer gear 522 configured to rotate and transfer torque from the second coupler gear 521 to a second splitter output shaft 520. The first output shaft 510 and second output shaft 520 shown separated by a distance and configured to adjust an expandable implant 1000 having two actuators 1030,1040 separated by a distance. As one with skill in the art may appreciate additional gears and shafts may be provided in accordance with known methods of stepping up the output torque, stepping down the output torque, and changing the distance separating the first splitter output shaft 510 and the second splitter output shaft 520.

FIG. 16 shows an expandable implant 1000 having a first endplate 1010, a second endplate 1020, a first actuator 1030 and a second actuator 1040, with the first actuator 1030 and the second actuator 1040 configured to change at least one of a height and an angle of lordosis between the first endplate 1010 relative to the second endplate 1020. An expansion driver 100 is shown including a splitter attachment 500, the splitter attachment 500 having a first splitter output shaft 510 configured to rotate the first actuator 1030 and a second splitter output shaft 520 configured to rotate the second actuator 1040.

Similar to the operation of expansion driver 100 described above, when a first amount of resistance from the first actuator 1030 on the first splitter output shaft 510 is less than a second amount of resistance from the second actuator 1040 on the second splitter output shaft 520, the first bevel gear 132 and the second bevel gear 133 of the expansion driver 100 are configured to rotate the first driver 110 of the expansion driver 100. The first driver 110 will in turn rotate all the internal gearing of the splitter attachment 500 operably connected between the first driver 110 and first splitter output shaft 510, and the first splitter output shaft 510 will rotate the first actuator 1030 to thereby adjust the expandable implant 1000. The second splitter output shaft 520 will not adjust the second actuator 1040 of the expandable implant 1000, and thus the first actuator 930 will continue to be rotated adjusting the angle of lordosis of the expandable implant 1000 until an equal amount of resistance is observed by the first actuator 1030 and the second actuator 1040.

FIG. 17 shows the expansion driver 100 having a splitter attachment 500, operably engaged with the expandable implant 1000 to adjust the expandable implant 1000. For expansion drivers similar to the embodiments described above, a rotation of a handle 130 will in turn rotate one or more of a first driver 110 and a second driver 120 of the expansion driver 100 depending on an amount of resistance thereon. Also as described above, when a splitter attachment 500 is integrated with an expansion driver 100, a rotation of the first driver 110 will rotate a first splitter output shaft 510 and a rotation of the second driver 120 will rotate a second splitter output shaft 520.

When a first amount of resistance from the first actuator 1030 on the first splitter output shaft 510 is more than a second amount of resistance of the second actuator 1040 on the second splitter output shaft 520, the first bevel gear 132 and the second bevel gear 133 of the expansion driver 100 are configured to rotate the second driver 120 of the expansion driver 100. The second driver 120 will in turn rotate all the internal gearing of the splitter attachment 500 operably connected between the second driver 120 and second splitter output shaft 520, and the second splitter output shaft 520 will rotate the second actuator 1040 to thereby adjust the expandable implant 1000. The first splitter output shaft 510 will not adjust the first actuator 1030, and thus the second actuator 1040 will continue to be rotated adjusting the angle of lordosis of the expandable implant 1000 until an equal amount of resistance is observed by the first actuator 1030 and the second actuator 1040.

When a first amount of resistance from the first actuator 1030 on the first splitter output shaft 510 is substantially equal to a second amount of resistance of the second actuator 1040 on the second splitter output shaft 520, the first bevel gear 132 and the second bevel gear 133 of the expansion driver 100 are configured to rotate both the first driver 110 and the second driver 120, which in turn rotate the first actuator 1030 and the second actuators 1040 of the expandable implant 1000.

FIG. 18 shows the expandable implant 1000 adjusted to an exemplary angle of lordosis by the expansion driver 100 having the splitter attachment 500. In the transition from the collapsed configuration of the expandable implant 1000 as seen in FIG. 16, to the expanded configuration of FIG. 18, it is implied that the amount of resistance experienced on the first end of the expandable implant 1000 was lower than the amount of resistance experienced on the second side of the expandable implant 1000. This would be similar to forces experienced within an intervertebral disc space of a patient, where a natural lordosis angle could be restored and the expandable implant 1000 subsequently evenly expanded to a desired height.

Exemplary embodiments herein have been directed to expandable implants configured for adjustment in height and angle of lordosis. It is contemplated that devices within the scope of this disclosure could be used to adjust expandable implants which are adjustable in height, length, width, angle of lordosis, and any change of dimension. The chosen embodiments should not be construed as limiting and this disclosure is intended to encompass the due bounds as presented in the claims.

What is claimed is:

1. An expansion driver configured to adjust an expandable implant, comprising:
    a first driver having a first gear disposed at a first end thereof, and a second end that is opposite the first end and configured to engage a first actuator of the expandable implant;
    a second driver having a second gear disposed at a first end thereof, and a second end that is opposite the first end and configured to engage a second actuator of the expandable implant, the first driver disposed about the second driver and the second gear opposing the first gear;
    a housing configured to enclose at least a portion of a shaft of the first driver and at least a portion of a shaft of the second driver;
    a handle disposed over the housing and having at least one bevel gear rotatably attached thereto, the at least one bevel gear configured to engage each of the first gear and the second gear; and
    a threaded cap configured to engage the handle to secure the first end of the first driver and the first end of the second driver within the handle;
    the handle being operably connected to the first gear of the first driver and the second gear of the second driver, wherein upon a rotation of the handle, a torque is applied to at least one of the first driver or the second driver, thereby adjusting the expandable implant.

2. The expansion driver of claim 1, wherein the housing includes at least one locking projection disposed on a distal end thereof, the at least one locking projection being configured to removably secure the expandable implant to the expansion driver.

3. The expansion driver of claim 2, wherein each locking projection of the at least one locking projection comprises a locking tab.

4. The expansion driver of claim 2, wherein the at least one locking projection includes two locking projections.

5. The expansion driver of claim 2, wherein the expansion driver is configured to be removably secured to the expandable implant prior to placement of the expandable implant into an intervertebral space of a patient.

6. The expansion driver of claim 5, wherein the expansion driver is configured to insert, place, and adjust a dimension of the expandable implant within the intervertebral space of the patient.

7. The expansion driver of claim 1, wherein the first driver is annularly disposed about the second driver.

8. The expansion driver of claim 7, wherein the first driver and the second driver are coaxial.

9. The expansion driver of claim 7, wherein the first driver is configured to rotate around the second driver, and the second driver is configured to rotate within the first driver.

10. The expansion driver of claim 1, wherein the first driver and the second driver are each configured to rotate independently of the other.

11. The expansion driver of claim 1, wherein the second end of the first driver includes a keyed shape configured to communicate with a complementary contact surface of the first actuator, and the second end of the second driver includes a keyed shape configured to communicate with a complementary contact surface of the second actuator of the expandable implant.

12. The expansion driver of claim 1, wherein the at least one bevel gear comprises a first bevel gear and a second bevel gear configured to engage the first gear and the second gear, respectively.

13. The expansion driver of claim 12, wherein the handle is configured such that upon the rotation of the handle, the torque is transferred from the handle to the first bevel gear and the second bevel gear,
    wherein the first bevel gear and the second bevel gear are configured to rotate the first driver and the second driver.

14. The expansion driver of claim 12, wherein when a first amount of resistance on the first driver is less than a second amount of resistance on the second driver, the first bevel gear and the second bevel gear are configured to rotate the first driver.

15. The expansion driver of claim 12, wherein when a first amount of resistance on the first driver is more than a second amount of resistance on the second driver, the first bevel gear and the second bevel gear are configured to rotate the second driver.

16. The expansion driver of claim 12, wherein when a first amount of resistance on the first driver is equal to a second amount of resistance on the second driver, the first bevel gear and the second bevel gear are configured to rotate both the first driver and the second driver.

17. The expansion driver of claim 1, wherein the housing is configured to enclose the first end of the first driver and the first end of the second driver.

18. The expansion driver of claim 1, wherein the expansion driver is configured to deliver one or more of simultaneous and equal amounts of torque to both the first actuator and the second actuator of the expandable implant, and wherein the expandable implant includes two independent expansion mechanisms to allow for independent expansion of a first portion and a second portion of the expandable implant.

* * * * *